(12) United States Patent
Tata

(10) Patent No.: US 10,188,492 B2
(45) Date of Patent: Jan. 29, 2019

(54) NAPKIN BAND WITH DENTAL FLOSS

(71) Applicant: Razvan Tata, Stratford, CT (US)

(72) Inventor: Razvan Tata, Stratford, CT (US)

( * ) Notice: Subject to any disclaimer, the term of this patent is extended or adjusted under 35 U.S.C. 154(b) by 53 days.

(21) Appl. No.: 15/584,145

(22) Filed: May 2, 2017

(65) Prior Publication Data

US 2018/0318054 A1 Nov. 8, 2018

(51) Int. Cl.
*A61C 15/04* (2006.01)
*A47G 21/16* (2006.01)

(52) U.S. Cl.
CPC ............ *A61C 15/043* (2013.01); *A47G 21/16* (2013.01); *A47G 2021/162* (2013.01)

(58) Field of Classification Search
CPC .... A61C 15/043; A61C 15/046; A47G 21/16; A47G 2021/162; Y10T 24/1312
See application file for complete search history.

(56) References Cited

U.S. PATENT DOCUMENTS

| | | | |
|---|---|---|---|
| 3,608,566 A | 9/1971 | Storandt | |
| 4,211,330 A | 7/1980 | Stock | |
| 4,467,503 A | 8/1984 | Boynton | |
| D289,973 S | 5/1987 | Corella | |
| 4,693,365 A | 9/1987 | Corella | |
| 4,852,728 A | 8/1989 | Court | |
| 4,986,289 A | 1/1991 | McWhorter | |
| 5,014,725 A | 5/1991 | Patscot | |
| 5,322,077 A | 6/1994 | Corella | |
| 5,787,907 A | 8/1998 | Endelson | |
| 7,152,280 B1 | 12/2006 | Taylor | |
| 8,348,050 B2 | 1/2013 | Grossman | |
| 2010/0086496 A1* | 4/2010 | Lafferty | A61C 15/02 424/48 |
| 2011/0113634 A1 | 5/2011 | Crisp | |
| 2012/0279644 A1 | 11/2012 | Reese | |
| 2012/0292214 A1* | 11/2012 | Ou | B65D 75/46 206/388 |
| 2013/0118940 A1 | 5/2013 | Grossman | |

FOREIGN PATENT DOCUMENTS

WO  WO2007003884 A2  1/2001

OTHER PUBLICATIONS

Blaine R. Copenheaver, International Search Report for PCT/US2018/028806, dated Jul. 12, 2018, ISA/US.

* cited by examiner

*Primary Examiner* — Robert Sandy
(74) *Attorney, Agent, or Firm* — Michael A. Blake

(57) ABSTRACT

A napkin band, the napkin band including: a generally rectangular portion; a sealed pocket located generally along the length of the rectangular portion; a length of dental floss located inside the pocket.

9 Claims, 2 Drawing Sheets

NAPKIN BAND WITH DENTAL FLOSS

TECHNICAL FIELD

The present invention relates to napkin bands, and more particularly the invention relates to napkin bands that hold a length of dental floss.

BACKGROUND

When diners eat out, such as going to restaurants, bar-b-ques, picnics, or anywhere else, they often wish they could remove food that may be stuck in their teeth after the meal. One solution is a restaurant may supply toothpicks, however, toothpicks are known to cause injury to the gums, and may not work well in removing food from between the teeth. Also, many restaurants do not carry toothpicks.

Thus there is a need for a device for that overcomes the above listed and other disadvantages.

SUMMARY OF THE INVENTION

The invention relates to a napkin band, the napkin band comprising: a generally rectangular portion; a sealed pocket located generally along the length of the rectangular portion; a length of dental floss located inside the pocket.

BRIEF DESCRIPTION OF THE DRAWINGS

The present disclosure will be better understood by those skilled in the pertinent art by referencing the accompanying drawings, where like elements are numbered alike in the several figures, in which.

DETAILED DESCRIPTION

Figure 1:
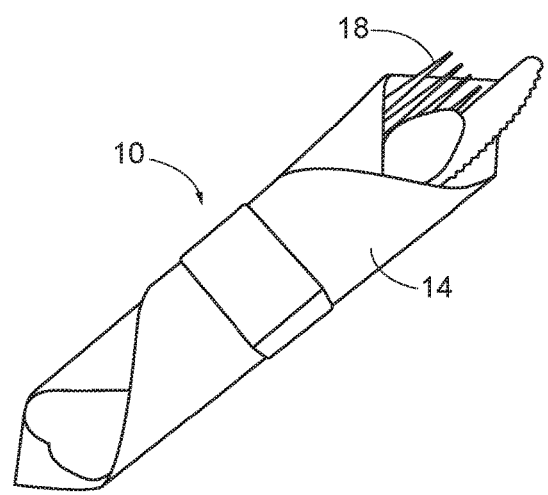
FIG. 1 is front view of the napkin band installed on utensil wrapped in a napkin.

FIG. 1 shows a front view of the napkin band 10. The napkin band 10 is shown holding a napkin 14 and silverware/plasticware 18 together.

Figure 2:
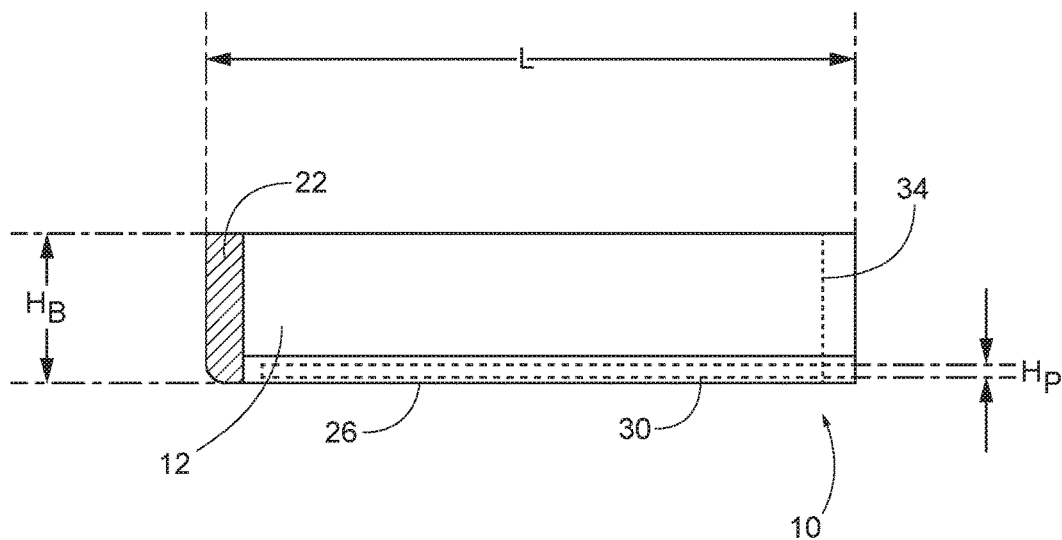
FIG. 2 is a front view of an unrolled napkin band.

FIG. 2 shows the napkin band 10 unrolled. The napkin band comprises a main generally rectangular portion 12. The napkin band 10 comprises a connecting means 22 at one end of the rectangular portion 12. In one embodiment, the connecting means 22 may be an adhesive strip located on the inside of the napkin band 10. The rectangular portion 12 has a longitudinal pocket 26 that holds a length of dental floss 30. The floss 30 is shown in dashed lines to indicate it is inside the pocket 26. The longitudinal pocket 26 may be formed by folding a portion of the rectangular portion 12 over itself and sealing it closed to form the longitudinal pocket 26. The pocket 26 may be sealed closed using an adhesive. The longitudinal pocket may be sealed such that the interior of the pocket 26 and the dental floss 30 is kept in a sanitary condition. The rectangular portion 12 has a length L, and a height $H_B$. The pocket 26 has a height $H_P$. The rectangular portion 12 may have an optional perforated portion 34. The perforated portion 34 may extend across the entire height of the band $H_B$. The perforated portion 34 may be near one end of the rectangular portion 12, or may be closer to the middle of the length L of the rectangular portion 12. In other embodiments, the perforated portion may just extend along the pocket 26, e.g. along the height of the pocket $H_P$. The napkin band may be made out of paper, plastic, or any other suitable material. In embodiments, without the perforated portion, the material should be one that can be easily ripped or torn by a user to access the dental floss 30 in the pocket 26.

Figure 3:
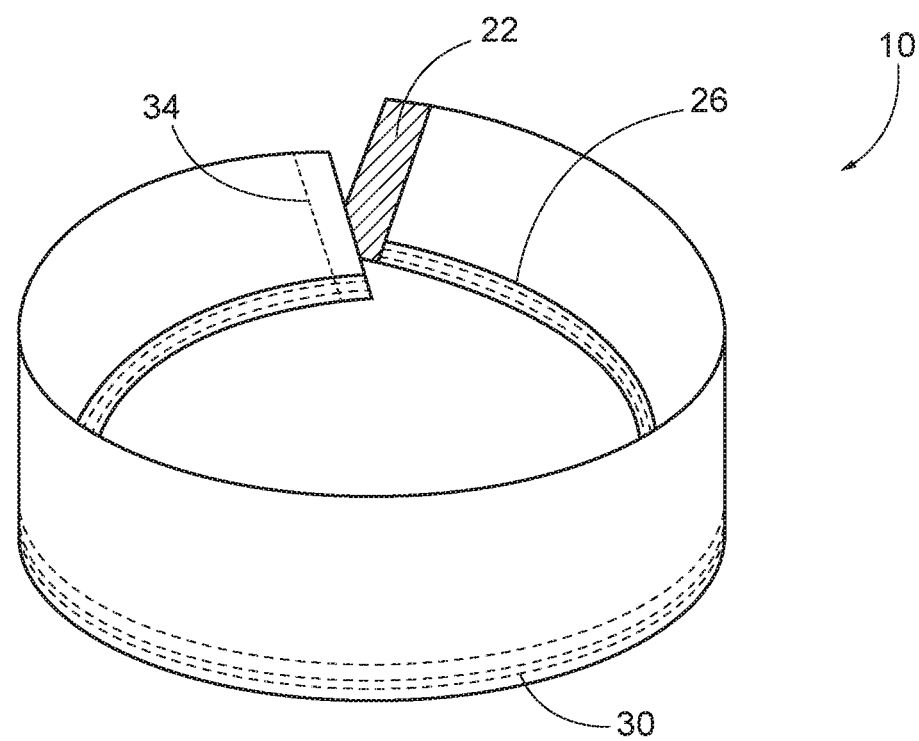
FIG. 3 is a perspective view of the napkin band showing how it may be attached to itself.

FIG. 3 shows a perspective view of the napkin band 10 with the adhesive strip 22 about to adhere to the outside of the napkin band 10.

The napkin band has many advantages. The invention is an improvement to a regular napkin band, in that it includes a pocket that runs along the length of the band when the band is unrolled. Inside the pocket will be a length of dental floss that the diner can use after his or her meal. In one embodiment, the diner can simply rip the band in half in order to access the dental floss in the pocket. In one embodiment the pocket may be made of the same material as the napkin band, simply folded over and attached to the napkin band with adhesive. An adhesive may be used to attach the napkin band to itself when it is wrapped around a napkin and utensils.

It should be noted that the terms "first", "second", and "third", and the like may be used herein to modify elements performing similar and/or analogous functions. These modifiers do not imply a spatial, sequential, or hierarchical order to the modified elements unless specifically stated.

While the disclosure has been described with reference to several embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiments disclosed as the best mode contemplated for carrying out this disclosure, but that the disclosure will include all embodiments falling within the scope of the appended claims.

What is claimed is:

1. A napkin band, the napkin band comprising:
   a generally rectangular portion;
   a sealed pocket located generally along the length of the rectangular portion;
   a length of dental floss located inside the sealed pocket; and
   wherein the sealed pocket is formed from a portion of the generally rectangular portion folded back upon the rectangular portion, and where the sealed pocket is sealed along its length and ends by an adhesive.

2. The napkin band of claim 1, wherein the rectangular portion has a height $H_B$ and the sealed pocket has a height $H_P$, and the height $H_B$ is greater than the height Hp.

3. The napkin band of claim 1, wherein the interior of the sealed pocket is sanitarily sealed such that the interior of the sealed pocket is sanitary.

4. The napkin band of claim 1, where the rectangular portion is made of paper.

5. The napkin band of claim 1, where the rectangular portion is made of plastic.

6. The napkin band of claim 1, further comprising printed information on the outside of the napkin band.

7. A napkin hand, the napkin hand comprising:
   a generally rectangular portion;
   a sealed pocket located generally along the length of the rectangular portion;
   a length of dental floss located inside the sealed pocket; and a perforated portion located near one end of the generally rectangular portion, the perforated portion intersecting the sealed pocket.

8. A napkin band, the napkin band comprising:
a generally rectangular portion;
a sealed pocket located generally along the length of the rectangular portion;
a length of dental floss located inside the sealed pocket; and
an adhesive strip at one end of the rectangular portion, the adhesive strip configured to attach the napkin band to attach to a napkin wrapped around one or more utensils.

9. A napkin band, the napkin band comprising:
a generally rectangular portion, wherein the rectangular portion has a height $H_B$;
a sealed pocket located generally along the length of the rectangular portion, the sealed pocket has a height $H_P$, and the height $H_B$ is greater than the height $H_P$;
a length of dental floss located inside the sealed pocket; and
a perforated portion that extends only along the height of the sealed pocket $H_P$.

\* \* \* \* \*